United States Patent [19]

Wiedermann

[11] 4,052,507

[45] Oct. 4, 1977

[54] PIPERIDINESULFONYLUREA DERIVATIVES

[75] Inventor: Hans E. Wiedermann, Niantic, Conn.

[73] Assignee: Pfizer Inc., New York, N.Y.

[21] Appl. No.: 726,126

[22] Filed: Sept. 24, 1976

Related U.S. Application Data

[62] Division of Ser. No. 629,771, Nov. 7, 1975, Pat. No. 3,998,828, which is a division of Ser. No. 546,003, Jan. 31, 1975, Pat. No. 3,936,445.

[51] Int. Cl.² ............................................. A61K 31/505
[52] U.S. Cl. .................................................... 424/251
[58] Field of Search ............................................ 424/251

[56] References Cited

U.S. PATENT DOCUMENTS

3,705,899  12/1972  Regniev et al. ............... 260/256.4

*Primary Examiner*—Jerome D. Goldberg
*Attorney, Agent, or Firm*—Connolly and Hutz

[57] ABSTRACT

A series of novel 1-piperidinesulfonylurea compounds derived from a pyrimidine monocarboxylic acid have been prepared by reacting an appropriate sulfamide with an organic isocyanate or a trisubstituted urea equivalent thereof. The sulfamylureas so obtained are useful in therapy as oral hypoglycemic agents. Typical members include those compounds derived from 1,3-dimethyl-1,2,3,4-tetrahydropyrimidine-2,4-dione-5-carboxylic acid, of which 1-(bicyclo[2.2.1]hept-5-en-2-yl-endo-methyl)-3-{4-[2-(1,3-dimethyl-1,2,3,4-tetrahydropyrimidine-2,4-dione-5-carboxamido)ethyl]-1-piperidinesulfonyl}urea is a most preferred embodiment.

12 Claims, No Drawings

PIPERIDINESULFONYLUREA DERIVATIVES

CROSS REFERENCE TO RELATED APPLICATIONS

This application is a division of application Ser. No. 629,771 filed Nov. 7, 1975 now U.S. Pat. No. 3,998,828 which is a division of application Ser. No. 546,003 filed Jan. 31, 1975 now U.S. Pat. No. 3,936,445.

BACKGROUND OF THE INVENTION

This invention relates to new and useful sulfamylurea derivatives, which are effective in reducing blood sugar levels to a remarkably high degree. More particularly, it is concerned with certain novel 4-substituted-1-piperidinesulfonylureas and their base salts with pharmacologically acceptable cations, which are useful in therapy as oral hypoglycemic agents for the treatment of diabetes.

In the past, various attempts have been made by numerous investigators in the field of organic medicinal chemistry to obtain new and better oral hypoglycemic agents. For the most part, these efforts have principally involved the synthesis and testing of various new and heretofore unavailable organic compounds, particularly in the area of the sulfonylureas. However, in the search for still newer and more improved oral hypoglycemic agents, far less is known about the activity of various heterocyclic sulfonylureas like 4-substituted-1-piperidinesulfonylureas and their derivatives. For instance, J. M. McManus et al. in the *Journal of Medicinal Chemistry*, Vol. 8, p. 766 (1965) report on several cyclic-sulfamylureas that are active, but none of these compounds possess any outstanding clinical advantages over that of either chlorpropamide or tolbutamide when used in this connection.

SUMMARY OF THE INVENTION

In accordance with the present invention, it has now been rather surprisingly found that certain novel 1-piperidinesulfonylureas (i.e., sulfamylureas) derived from a pyrimidine monocarboxylic acid are extremely useful when employed as oral hypoglycemic agents for the treatment of diabetic subjects. The novel sulfamylurea compounds of this invention are all selected from the group consisting of 1-piperidinesulfonylureas of the formula:

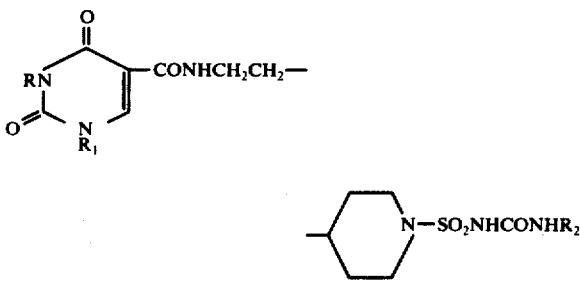

and the base salts thereof with pharmacologically acceptable cations, wherein R and $R_1$ are each alkyl having from one to three carbon atoms, and $R_2$ is a member selected from the group consisting of bicyclo[2.2.1]-hept-5-en-2-yl-endo-methyl, bicyclo[2.2.1]hept-2-yl-endo-methyl, 7-oxabicyclo[2.2.1]hept-2-yl-endo-methyl, 1-adamantyl and cycloalkyl having from five to eight carbon atoms. These compounds are all useful in lowering blood sugar levels when administered by the oral route of administration.

Of especial interest in this connection are such typical and preferred member compounds of the invention as 1-(bicyclo[2.2.1]hept-5-en-2-yl-endo-methyl-3-{4-[2-(1,3-dimethyl-1,2,3,4-tetrahydropyrimidine-2,4-dione-5-carboxamido)ethyl]-1-piperidinesulfonyl}urea, 1-(bicyclo[2.2.1]hept-2-yl-endo-methyl)-3-{4-[2-(1,3-dimethyl-1,2,3,4-tetrahydropyrimidine-2,4-dione-5-carboxamido)ethyl]-1-piperidinesulfonyl}urea, 1-(7-oxabicyclo[2.2.1]hept-2-yl-endo-methyl)-3-{4-[2-(1,3-dimethyl-1,2,3,4-tetrahydropyrimidine-2,4-dione-5-carboxamido)ethyl]-1-piperidinesulfonyl}urea, 1-(1-adamantyl)-3-{4-[2-(1,3-dimethyl-1,2,3,4-tetrahydropyrimidine-2,4-dione-5-carboxamido)ethyl]-1-piperidinesulfonyl}urea, 1-cyclohexyl-3-{4-[2-(1,3-dimethyl-1,2,3,4-tetrahydropyrimidine-2,4-dione-5-carboxamido)ethyl]-1-piperidinesulfonyl}urea and 1-(bicyclo[2.2.1]hept-5-en-2-yl-endo-methyl-3-{4-[2-(1-n-propyl-3-ethyl-1,2,3,4-tetrahydropyrimidine-2,4-dione-5-carboxamido)ethyl]-1-piperidinesulfonyl}urea, and their corresponding sodium salts. These particular compounds are all highly potent as regards their hypoglycemic activity.

DETAILED DESCRIPTION OF THE INVENTION

In accordance with the process employed for preparing the novel compounds of this invention, an appropriately substituted sulfamide compound of the formula:

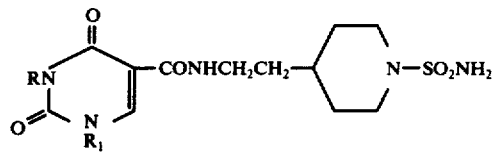

is reacted with an organic isocyanate reagent of the formula $R_2NCO$ wherein $R_2$ corresponds to the previously defined 1-substituent on the urea moiety of the desired final product. In this way, the corresponding 1-piperidinesulfonylurea compound is formed where R and $R_1$ on the pyrimidine moiety are each defined as previously indicated. This particular reaction is normally conducted in a basic solvent medium, most desirably employing an aprotic organic solvent such as tetrahydrofuran, dimethylsulfoxide or dimethylformamide and preferably using a slight excess in moles of a base, like triethylamine or sodium hydride in mineral oil, etc. Many of the aforesaid isocyanate reagents ($R_2NCO$) are either known compounds or else they can easily be prepared, using methods well-known to those skilled in the art starting from readily available materials. In practice, it is usually preferable to employ at least about a molar equivalent of the isocyanate reagent in the aforesaid reaction of the present invention, with best results often being achieved by using a slight excess of same. Any temperature below that of reflux may be used in order to effect the reaction, which normally requires a time period of anywhere from several minutes up to about 24 hours depending, of course, upon the particular 1-piperidinesulfonylurea being prepared as well as the actual temperature of the reaction. Upon completion of this step, the product is easily isolated from the spent mixture in a most conventional fashion, e.g., by pouring same into an excess of anhydrous diethyl ether, whereby the desired 1-piperidinesulfonylurea readily precipitates in salt form from said mixture and is subsequently collected by such means as suction filtration and the like. Conversion to the free acidic compound then follows in due course in accordance with the classical methods of organic chemistry.

Another method for preparing the subject compounds of this invention involves reacting a 1-piperidinesulfamide in the form of an alkali metal or alkaline-earth metal salt (either employed as such or else formed in situ) with an appropriate 1,1,3-trisubstituted urea of the formula $(R')_2NCONHR_2$, wherein $R'$ is an aryl group such as phenyl, p-chlorophenyl, p-bromophenyl, p-nitrophenyl, p-acetylaminophenyl, p-tolyl, p-anisyl, α-naphthyl, β-naphthyl, and the like. This reaction is preferably carried out in the presence of a neutral polar organic solvent medium. Typical organic solvents for use in this connection include the N,N-dialkyl lower alkanoamides like dimethylformamide, dimethylacetamide, diethylformamide and diethylacetamide, as well as lower dialkyl sulfoxides such as dimethyl sulfoxide, diethyl sulfoxide and di-n-propyl sulfoxide, etc. It is desirable that the aforesaid solvent for this reaction be present in sufficient amount to dissolve each of the previously mentioned starting materials. In general, the reaction is conducted at a temperature that is in the range of from about 20° C. up to about 150° C. for a period of about 0.5 to about 24 hours. The relative amounts of reagents employed are such that the molar ratio of 1-piperidinesulfamide to the 1,1-diaryl-3-(monosubstituted)urea is most desirably in the preferred range of from about 1:1 to about 1:2, respectively. Recovery of the desired product from the reaction mixture is then achieved by first diluting the reaction solution with water and then adjusting if necessary the pH of the resulting solution to a value of at least about 8.0, followed by subsequent extraction of the basic aqueous solution with any water-immiscible organic solvent in order to remove the diarylamine byproduct of formula $(R')_2NH$ as well as minor amounts of unreacted or excess starting material that might possibly be present at this stage. Isolation of the desired 1-piperidinesulfonylurea from the basic aqueous layer then follows in due course, viz., by adding a sufficient amount of a dilute aqueous acid solution to cause precipitation of the desired sulfamylurea to occur.

The two major type starting materials required for this reaction, viz., the 1-piperidinesulfamides and the 1,1-diaryl-3-(monosubstituted)ureas, are both readily prepared by those skilled in the art in accordance with the conventional methods of organic chemistry. For instance, the 1-piperidinesulfamides, which are novel compounds and are also used as starting materials in the previously described isocyanate method, are suitably obtained by using classical methods of synthesis starting from the known 4-(2-aminoethyl)pyridine and proceeding in accordance with standard organic procedure as hereinafter described in the experimental section of this specification in some detail (see Preparations A-F and Examples I-III). The 1,1-diaryl-3-(monosubstituted)-ureas, on the other hand, are all readily prepared from common organic reagents by employing standard procedures well known in the art, e.g., the desired 1,1,3-trisubstituted urea may be prepared from the corresponding disubstituted carbamyl chloride $[(R')_2NCOCl]$ and the appropriate amine $(R_2BH_2)$ in accordance with the general procedure of J. F. L. Reudler, as described in *Recueil des Travaux Chimiques des Pays-Bas*, Vol. 33, p. 64 (1914).

The chemical bases which are used as reagents in this invention to prepare the aforementioned pharmaceutically acceptable base salts are those which form non-toxic salts with the many herein described acidic 1-piperidinesulfonylureas, such as 1-(bicyclo[2.2.1]hept-5-en-2-yl-endo-methyl)-3-{4-[2-(1.3-dimethyl-1,2,3,4-tetrahydropyrimidine-2,4-dione-4-carboxamido)ethyl]-1-piperidinesulfonyl}urea, for example. These particular non-toxic base salts are of such nature that their cations are said to be essentially non-toxic in character over the wide range of dosage administered. Examples of such cations include those of sodium, potassium, calcium and magnesium, etc. These salts can easily be prepared by simply treating the aforementioned 1-piperidinesulfonylureas with an aqueous solution of the desired pharmacologically acceptable cations, and then evaporating the resulting solution to dryness while preferably being placed under reduced pressure. Alternatively, they may also be prepared by mixing lower alkanolic solutions of the said acidic compounds and the desired alkali metal alkoxide together, and then evaporating the resulting solution in the same manner as before. In either case, stoichiometric amounts of reagents must be employed in order to ensure completeness of reaction and maximum production of yields with respect to the desired final product.

As previously indicated, the 1-piperidinesulfonylurea compounds of this invention are all readily adapted to therapeutic use as oral hypoglycemic agents, in view of their ability to lower the blood sugar levels of diabetic and non-diabetic subjects to a statistically significant degree. For instance, 1-(bicyclo[2.2.1]hept-5-en-2-yl-endo-methyl)-3-{4-[2-(1,3-dimethyl-1,2,3,4-tetrahydropyrimidine-2,4-dione-5-carboxamido)ethyl]-1-piperidinesulfonyl}urea (as the sodium salt), a typical and preferred agent of the present invention, has been found to consistently lower blood sugar levels in the normal fasted rat (as well as in fed rats and dogs) to a statistically significant degree when given by the intraperitoneal route of administration at dose levels ranging from 1.0 mg./kg. to 15 mg./kg., respectively, without showing any substantial signs of toxic side effects. The other compounds of this invention also cause similar results. Furthermore, all the herein described compounds of this invention can be administered orally, for the present purposes at hand, without causing any significant untoward pharmacological side reactions to occur in the subject to whom they are so administered. In general, these compounds are ordinarily administered at dosage levels ranging from about 0.1 mg. to about 2.5 mg. per kg. of body weight per day, although variations will necessarily occur depending upon the condition and individual response of the subject being treated and the particular type of oral formulation chosen.

In connection with the use of the 1-piperidinesulfonylurea compounds of this invention for the treatment of diabetic subjects, it is to be noted that they may be administered either alone or in combination with pharmaceutically acceptable carriers and that such administration can be carried out in both single and multiple dosages. More particularly, the novel compounds of the invention can be administered in a wide variety of different dosage forms, i.e., they may be combined with various pharmaceutically acceptable inert carriers in the form of tablets, capsules, lozenges, troches, hard candies, powders, aqueous suspension, elixirs, syrups and the like. Such carriers include solid diluents or fillers, sterile aqueous media and various non-toxic organic solvents, etc. Moreover, such oral pharmaceutical compositions can be suitably sweetened and/or flavored by means of various agents of the type commonly employed for just such a purpose. In general, the therapeutically-effective compounds of this invention are present in such dosage forms at concentration levels ranging from about 0.5% to about 90% by weight of the total composition, i.e., in amounts which are sufficient to provide the desired unit dosage.

For purposes of oral administration, tablets containing various excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include the high molecular weight polyethylene glycols. When aqueous suspensions and/or elixirs are desired for oral administration, the essential active ingredient therein may be combined with various sweetening or flavoring agents, coloring matter or dyes and, if so desired, emulsifying and/or suspending agents as well, together with such diluents as water, ethanol, propylene glycol, glycerin and various like combinations thereof.

The activity of the compounds of the present invention, as hypoglycemic agents, is determined by their ability to lower blood sugar levels in the normal fasted rat when tested therein for such purposes according to the procedure described by W. S. Hoffman, as reported in the *Journal of Biological Chemistry*, Vol. 120, p. 51 (1937). The latter method measures directly the amount of glucose in the blood at any given time and from this, the maximum percent decrease in blood sugar can be readily calculated and reported as hypoglycemic activity per se. In this way, the present 1-piperidinesulfonylurea compounds are shown to markedly reduce the blood sugar levels of non-anesthetized rats when administered to them at dose levels as low as 1.0 mg./kg.

PREPARATION A

To a rapidly-stirred solution consisting of 148.1 g. (1.0 mole) of phthalic anhydride dissolved in 1000 ml. of xylene and also containing 13 ml. of triethylamine, there was slowly added in a dropwise manner 122.1 g. (1.0 mole) of 4-(2-aminoethyl)pyridine [L. E. Brady et al., Journal of Organic Chemistry, Vol. 26, p. 4758 (1961)] dissolved in 1000 ml. of xylene. The reaction was slightly exothermic in nature and a heavy orange-yellow gum was observed to precipitate from the stirred system toward the end of the addition step. Upon completion of the addition, the resulting reaction mixture was refluxed for a period of approximately two hours (using a Dean-Stark trap to remove the water therefrom) and there was thus obtained a completely homogeneous yellow liquid. The latter liquid was then decanted while still hot into a 2-liter Erlenmeyer Flask and slowly allowed to crystallized on cooling to room temperature (~25° C.). In this manner, there were ultimately obtained 209 g. (83%) of crystalline 4-(2-phthalimidoethyl)pyridine in the form of a white solid material melting at 155°–157° C.

Anal. Calcd. for $C_{15}H_{12}N_2O_2$: C, 71.41; H, 4.80; N, 11.11. Found: C, 71.55; H, 4.91; N, 10.75.

A 15-gal. autoclave was charged with 1.8 kg. (7.13 moles) of 4-(2-phthalimidoethyl)pyridine, 10.62 gal. of anhydrous methanol saturated with dry hydrogen chloride gas and 72.2 g. of platinum oxide catalyst. The autoclave and its contents were then placed under 200 p.s.i. pressure of hydrogen, while at 50° C. and held at that point until 95% of the theoretical hydrogen uptake was complete (this required approximately 4.33 hours). At the end of this time, the reaction mixture was cooled to 24° C., vented and then purged with nitrogen. After removal of the catalyst by means of filtration, the resulting filtrate was concentrated in vacuo to a final volume of ca. 3.0 liters and the solid product, which had precipitated from the residual liquid during the course of the concentration step, was then recovered by means of collecting same on a filter funnel with the aid of suction filtration. Upon washing with isopropanol and air-drying to constant weight, there was obtained 1070 g. (51%) of crystalline 4-(2-phthalimidoethyl)piperidine hydrochloride in the form of a pure white solid (m.p. 235°–242° C.). Recrystallization from ethanol-diethyl ether then raised the melting point to 240°–242° C. (analytical sample).

Anal. Calcd. for $C_{15}H_{18}N_2O_2 \cdot HCl$: C, 61.07; H, 6.49; N, 9.50. Found: C, 60.79; H, 6.37; N, 9.43.

A 12-liter three-necked, round-bottomed flask was charged with 1700 g. (5.69 mole) of 4-(2-phthalimidoethyl)piperidine hydrochloride, 552 g. (5.69 mole) of sulfamide and 5.8 liters of pyridine. The resulting reaction mixture was then stirred under the reflux conditions for a period of 24 hours and finally cooled to room temperature (~25° C.). The cooled mixture was next poured into an ice-water mixture (36 liters) and stirred for an additional period of 30 minutes. At this point, the precipitated product was collected by means of suction filtration, washed with 5.0 liters of 0.1N hydrochloric acid, then with 15 liters of water and finally with 3.0 liters of cold ethanol. After air-drying to constant weight, there was obtained a 1326 g. (71%) yield of pure 4-(2-phthalimidoethyl)-1-piperidinesulfonamide, m.p. 195°–197° C. Recrystallization from ethanol then gave the analytical sample as a white solid material (m.p. 202°–203° C.).

A 1-liter round-bottomed flask was charged with 28.4 g. (0.084 mole) of 4-(2-phthalimidoethyl)-1-piperidinesulfonamide, 2.7 g. (0.084 mole) of anhydrous hydrazine and 250 ml. of methanol. The resulting white suspension was stirred and then refluxed for a period of 90 minutes, followed by removal of the most of the methanol via fractional distillation. At this point, the reaction mixture was observed to be a homogeneous yellow solution. Concentrated hydrochloric acid (350 ml.) was then added, and the resulting mixture was refluxed for an additional period of three hours before being cooled to room temperature. The insoluble by-product, which appeared at this point as a precipitate, was then removed by means of suction filtration and the resulting filtrate was thereafter evaporated to near dryness while under reduced pressure to give a white solid material as the final residual product. The latter was subsequently triturated with hot acetone, filtered and air dried to constant weight to afford 18.5 g. (91%) of pure 4-(2-aminoethyl)-1-piperidinesulfonamide hydrochloride, m.p. 188°-192° C. Recrystallization from ethanol then gave the analytical sample (m.p. 195°-197° C.).

Anal. Calcd. for $C_7H_{17}N_3O_2S.HCl$: C, 34.49; H, 7.44; N, 17.24. Found: C, 34.56; H, 7.45; N, 17.24.

PREPARATION B

A suspension of 9.2 g. (0.05 mole) of 1,3-dimethyl-1,2,3,4-tetrahydropyrimidine-2,4-dione-5-carboxylic acid [C. W. Whitehead, *Journal of the American Chemical Society*, Vol. 74, p. 4267 (1952)] in 50 ml. of carbon tetrachloride and 70 ml. of thionyl chloride was heated on a steam bath for a period of 45 minutes. At the end of this time, the clear solution so obtained was concentrated in vacuo and excess thionyl chloride was then removed by adding 100 ml. of benzene to the solution and subsequently evaporating the resulting mixture to dryness while under reduced pressure. This particular purification step was repeated again and there was ultimately obtained pure 1,3-dimethyl-1,2,3,4-tetrahydropyrimidine-2,4-dione-5-carboxylic acid chloride in the form of a white crystalline residue, which was used as such in the next reaction step without any further purification being necessary. The yield of the acid chloride product was nearly quantitative.

PREPARATION C

A suspension of 2.3 g. (0.01 mole) of 1-n-propyl-3-ethyl-1,2,3,4-tetrahydropyrimidine-2,4-dione-5-carboxylic acid [prepared according to the method of C. W. Whitehead, *Journal of the American Chemical Society*, Vol. 74, p. 4267 (1952)] in 10 ml. of carbon tetrachloride and 10 ml. of thionyl chloride was heated on a steam bath until evolution of both hydrogen chloride and sulfur dioxide gas subsided. Removal of the solvent and excess thionyl chloride from the mixture was then accomplished by concentrating same in vacuo, followed by the addition of 50 ml. of benzene to the residue in order to remove any remaining traces of thionyl chloride. The resulting mixture was then evaporated to dryness while under reduced pressure and after repeating the entire purification procedure three times, there was ultimately obtained pure 1-n-propyl-3-ethyl-1,2,3,4-tetrahydropyrimidine-2,4-dione-5-carboxylic acid chloride in the form of a pale yellow crystalline residue. The latter material was used in the next reaction step without any further purification being necessary. The yield of said acid chloride product was quantitative.

PREPARATION D

The procedure described in Preparations B-C is repeated here to prepare the following 1,3-dialkyl-1,2,3,4-tetrahydropyrimidine-2,4-dione-5-carboxylic acid chlorides, starting from the corresponding acid in each case:

1-methyl-3-ethyl-1,2,3,4-tetrahydropyrimidine-2,4-dione-5-carboxylic acid chloride 1-methyl-3-isopropyl-1,2,3,4-tetrahydropyrimidine-2,4-dione-5-carboxylic acid chloride 1-ethyl-3-methyl-1,2,3,4-tetrahydropyrimidine-2,4-dione-5-carboxylic acid chloride 1,3-diethyl-1,2,3,4-tetrahydropyrimidine-2,4-dione-5-carboxylic acid chloride 1-ethyl-3-n-propyl-1,2,3,4-tetrahydropyrimidine-2,4-dione-5-carboxylic acid chlorde 1-isopropyl-3-methyl-1,2,3,4-tetrahydropyrimidne-2,4-dione-5-carboxylic acid chloride 1,3-di-n-propyl-1,2,3,4-tetrahydropyrimidne-2,4-dione-5-carboxylic acid chloride

PREPARATION E

A 500 ml. three-necked, round bottomed flask was charged with 14.6 g. (0.119 mole) of endo-2-aminomethylbicyclo[2.2.1]hept-5-ene [P. Wilder et al., Journal of Organic Chemistry, Vol. 30, p. 3078 (1965)], 18.0 g. (0.178 mole) of triethylamine and 100 ml. of tetrahydrofuran. The mixture was then rapidly cooled and stirred in an ice bath, while a solution consisting of 27.4 g. (0.119 mole) of N,N-diphenylcarbamoyl chloride dissolved in 100 ml. of tetrahydrofuran was slowly added thereto in a dropwise manner. After the addition was complete, the reaction mixture was stirred at room temperature (~25° C.) for a period of one hour and the resulting solution was then concentrated in vacuo (to approximately one-third of its original volume) to remove most of the tetrahydrofuran. On cooling, there was obtained a crystalline precipitate, which was subsequently collected by means of suction filtration and thereafter suspended in 250 ml. of 1N aqueous hydrochloric acid. Extraction of the latter aqueous solution with three 200-ml. portions of chloroform, followed by drying of the combined organic extracts then gave a clear organic solution upon filtration. After evaporating the clear filtrate to near dryness while under reduced pressure, there was ultimately obtained a heavy viscous oil, which subsequently crystallized on trituration with n-hexane. Recrystallization of this latter material from diethyl ether/n-hexane then gave pure 1,1-diphenyl-3-(bicyclo[2.2.1]hept-5-en-2-yl-endo-methyl)urea, m.p. 129°-130° C. The analytical sample was a crystalline white solid.

Anal. Calcd. for $C_{21}H_{22}N_2O$: C, 79.21: H, 6.96; N, 8.80. Found: C, 79.19; H, 7.05; N, 8.93.

PREPARATION F

A 3-liter round-bottomed flask was charged with 212 g. (4.0 moles) of acrylonitrile, 272 g. (4.0 moles) of furan and 50 mg. of hydroquinone all dissolved in a total of one liter of dry benzene. Stirring was then commenced, while a solution consisting of 55 ml. (0.5 mole) of titanium tetrachloride dissolved in 500 ml. of benzene was added at such a rate that the temperature did not exceed 35° C. The resulting mixture was then stirred at room temperature (~25° C.) for a period of five days in order to complete the reaction, followed by treatment with 500 ml. of 0.5N hydrochloric acid. After filtering the acidified mixture, the benzene layer was collected and subsequently saved, while the aqueous layer was extracted anew with a fresh portion of benzene. At this point, the organic layers were combined, washed with water and then dried over anhydrous magnesium sulfate. After removal of the drying agent by means of suction filtration and the organic solvent by means of evaporation under reduced pressure, there was obtained 156.3 g. (32%) of 7-oxabicyclo[2.2.1]hept-5-en-2-ylnitrile in the form of a crude mixture of endo- and exo-isomers.

The above crude mixture (130 g.) was then hydrogenated in 1000 ml. of acetone at 50 p.s.i. pressure, using 2 g. of palladium-on-barium sulfate as catalyst. After removal of the catalyst by means of suction filtration and the solvent by means of evaporation under reduced pressure, there was obtained a residual liquid which on fractional distillation gave 55.5 g. (42%) of pure endo-7-oxabicyclo[2.2.1]hept-2-ylnitrile (b.p. 45° C./0.1 mm. Hg) and 37.9 g. (29%) of pure exo-7-oxabicyclo[2.2.1]- hept-2-ylnitrile (b.p. 48° C./0.02 mm.Hg) plus 14.7 g. (11%) of an endo/exo mixture.

Anal. Calcd. for $C_7H_9NO$: C, 68.27; H, 7.37; N, 11.37. Found: (endo): C, 67.96; H, 7.21; N, 11.37. (exo): C, 68.32; H, 7.42; N, 11.64.

To a well-stirred solution consisting of 54.3 g. (9.44 mole) of endo-7-oxabicyclo[2.2.1]hept-2-ylnitrile dissolved in 500 ml. of methanol, there were added 24 ml. of a slurry of Raney nickel in methanol, followed by the dropwise addition of 33.2 g. (0.88 mole) of sodium borohydride dissolved in 110 ml. of 4N aqueous sodium hydroxide. The latter step was carried out with the aid of external cooling so as to keep the temperature of the reaction mixture within the 40°-50° C. range. After the addition was complete (and this required approximately 25 minutes), the mixture was further stirred at ambient temperatures (i.e., without cooling) for a period of 20 minutes, at which point no further gas evolution could be detected. The spent reaction mixture was then filtered to remove solid impurities, and the resulting filtrate thereafter concentrated in vacuo to afford a residue that was subsequently suspended in 500 ml. of 1N aqueous sodium hydroxide. After extracting the latter basic aqueous solution three times with chloroform, the chloroform extracts were combined, dried over anhydrous magnesium sulfate and thereafter evaporated to constant volume while under reduced pressure to give 55.5 g. (100%) of endo-7-oxabicyclo[2.2.1]hept-2-ylmethylamine (b.p. 90° C./10 mm. Hg.), which was used as such in the next reaction step without any further purification being necessary.

The procedure described in Preparation E was now repeated to prepare the 1,1-diphenyl-3-(monosubstituted)urea compound except that endo-7-oxabicyclo[2.2.1]hept-2-ylmethylamine obtained as described above was the appropriate amine starting material employed in place of endo-2-aminomethylbicyclo[2.2.1]hept-5-ene, again using the same molar proportions as before. In this particular case, the corresponding final product thus obtained was 1,1-diphenyl-3-(7-oxabicyclo[2.2.1]hept-2-yl-endo-methyl)-urea, m.p. 109°-111° C.

Anal. Calcd. for $C_{20}H_{22}N_2O_2$: C, 74.49; H, 6.89; N, 8.68. Found: C, 74.28; H, 6.93; N, 8.61.

EXAMPLE I

To a mixture of 12.1 g. (0.05 mole) of 4-(2-aminoethyl)-1-piperidinesulfonamide hydrochloride and 10.2 g. (0.10 mole) of triethylamine in 100 ml. of dry tetrahydrofuran, there was added the product of Preparation B (viz., 1,3-dimethyl-1,2,3,4-tetrahydropyrimidine-2,4-dione-5-carboxylic acid chloride) suspended in 50 ml. of tetrahydrofuran. The reaction mixture was then stirred at ambient temperatures for a period of approximately 16 hours. At the end of this time, the precipitated solids which formed were subsequently recovered by means of suction filtration and thereafter thoroughly digested with 200 ml. of water. The insoluble product was then collected again on the filter funnel and air-dried to constant weight, followed by recrystallization from 200 ml. of acetone to give 17 g. (94%) of pure 4-[2-(1,3-dimethyl-1,2,3,4-tetrahydropyrimidine-2,4-dione-5-carboxamido)ethyl]-1-piperidinesulfonamide, m.p. 201°-202° C.

Anal. Calcd. for $C_{13}H_{23}N_5O_5S$: C, 45.03; H, 6.14; N, 19.38. Found: C, 45.33; H, 6.14; N, 19.45.

EXAMPLE II

To a mixture of 2.4 g. (0.01 mole) of 4-(2-aminoethyl)-1-piperidinesulfonamide hydrochloride and 2.0 g. (0.02 mole) of triethylamine in 25 ml. of dry tetrahydrofuran, there was added the product of Preparation C (viz., 1-n-propyl-3-ethyl-1,2,3,4-tetrahydropyrimidine-2,4-dione-5-carboxylic acid chloride) suspended in 25 ml. of dry tetrahydrofuran. The reaction mixture was then stirred at ambient temperatures for a period of approximately 16 hours. At the end of this time, the crystalline precipitate of triethylamine hydrochloride was removed by suction filtration and the resulting filtrate was thereafter evaporated to dryness under reduced pressure to give 4.0 g. of crude 4-[2-(1-n-propyl-3-ethyl-1,2,3,4-tetrahydropyrimidine-2,4-dione-5-carboxamido)ethyl]-1-piperidinesulfonamide in the form of a yellow colored gum. The latter material was then recrystallized from acetonitrile and there was ultimately obtained (after three recrystallizations) 2.0 g. of pure product, viz., 4-[2-(1-n-propyl-3-ethyl-1,2,3,4-tetrahydropyrimidine-2,4-dione-5-carboxamido)ethyl]-1-piperidinesulfonamide in the form of white needles melting at 164°-165.5° C. The yield of pure product amounted to 47%.

Anal. Calcd. for $C_{17}H_{23}N_5O_5S$: C, 49.14; H, 7.03; N, 16.86. Found: C, 49.01; H, 6.89; N, 16.89.

EXAMPLE III

The procedure described in Examples I-II is repeated to prepare the following 1-piperidinesulfamides by simply using the appropriate 1,3-dialkyl-1,2,3,4-tetrahydropyrimidine-2,4-dione-5-carboxylic acid chloride as the requisite starting material of choice in each instance:

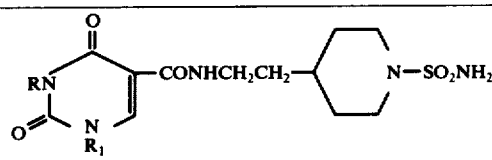

| R | $R_1$ |
|---|---|
| $C_2H_5$ | $CH_3$ |
| iso-$C_3H_7$ | $CH_3$ |
| $CH_3$ | $C_2H_5$ |
| $C_2H_5$ | $C_2H_5$ |
| n-$C_3H_7$ | $C_2H_5$ |
| $CH_3$ | iso-$C_3H_7$ |
| n-$C_3H_7$ | n-$C_3H_7$ |

EXAMPLE IV

A mixture of 2.8 g. (0.0075 mole) of 4-[2-(1,3-dimethyl-1,2,3,4-tetrahydropyrimidine-2,4-dione-5-carboxamido)ethyl]-1-piperidinesulfonamide, 2.4 g. (0.0075 mole) of 1,1-diphenyl-3-bicyclo[2.2.1]hept-5-en-2-yl-endo-methyl)urea and 0.34 g. (0.0075 mole) of 56% sodium hydride (in mineral oil) in 15 ml. of dry N,N-dimethylformamide was heated to 70° C. for a period of one hour. The clear solution so obtained was then cooled and subsequently poured into 200 ml. of diethyl ether, followed by recovery of the resulting crystalline precipitate via suction filtration. The filter cake was then washed well with diethyl ether and thereafter dissolved in 50 ml. of water. Upon acidification with 10 ml. of 6N hydrochloric acid and extraction into chloroform (three-50 ml. portions were required), followed by decolorization with charcoal and drying over anhydrous magnesium sulfate, there was finally obtained a clear chloroform solution of the desired product. Evaporation of the latter solution to near dryness while under reduced pressure then gave a crystalline residue, which was subsequently recrystallized from 350 ml. of acetonitrile to give 2.2 g. (57%) of pure 1-(bicyclo-[2.2.1]hept-5-en-2-yl-endo-methyl)-3-{4-[2-(1,3-dimethyl-1,2,3,4-tetrahydropyrimidine-2,4-dione-5-carboxamido)ethyl]-1-piperidinesulfonyl}urea, m.p. 216°–217° C.

Anal. Calcd. for $C_{23}H_{34}N_6O_6S$: C, 52.86; H, 6.65; N, 16.08. Found: C, 52.74; H, 6.50; N, 16.65.

EXAMPLE V

A mixture of 1.0 g. (0.002 mole) of 1-(bicyclo[2.2.1]-hept-5-en-2-yl-endo-methyl-3-{4-[2-(1,3-dimethyl-1,2,3,4-tetrahydropyrimidine-2,4-dione-5-carboxamido)ethyl]-1-piperidinesulfonyl}urea and 0.20 g. of 5% palladium-on-carbon catalyst in 300 ml. of tetrahydrofuran was hydrogenated on a Parr shaker at 40 p.s.i. pressure until no further hydrogen uptake could be detected. The catalyst was then separated from the mixture by means of filtration and the resulting filtrate thereafter evaporated to dryness under reduced pressure. In this manner, there was obtained a crude residual product which after recrystallization from acetonitrile afforded pure 1-(bicyclo[2.2.1]hept-2-yl-endo-methyl)-3-{4-[2-(1,3-dimethyl-1,2,3,4-tetrahydropyrimidine-2,4-dione-5-carboxamido)ethyl]-1-piperidinesulfonyl}urea (m.p. 211.5°–212.5° C.) in 74% yield.

Anal. Calcd. for $C_{23}H_{36}N_6O_6S.O.5H_2O$ C, 51.76; H, 6.99; N, 15.75. Found: C, 51.89; H, 6.71; N, 16.01.

EXAMPLE VI

A mixture consisting of 750 mg. (0.002 mole) of 4-[2-(1,3-dimethyl-1,2,3,4-tetrahydropyrimidine-2,4-dione-5-carboxamido)-ethyl]-1-piperidinesulfonamide, 280 mg. (0.002 mole) of cyclohexyl isocyanate and 90 mg. (0.002 mole) of 56.6% sodium hydride (dispersed in mineral oil) in 10 ml. of dry N,N-dimethylformamide was stirred at ambient temperatures for a period of 14 hours. At the end of this time, the mixture was poured into 300 ml. of anhydrous diethyl ether and the white crystalline precipitate which formed at this point was subsequently recovered by means of suction filtration and washed well with fresh diethyl ether prior to being dissolved in 1N aqueous hydrochloric acid. The latter aqueous solution was then extracted with chloroform and the chloroform extracts thereafter separated from the aqueous layer, washed well with water and then finally with a saturated solution of aqueous sodium chloride. After drying the chloroform solution over anhydrous magnesium sulfate, followed by decolorization with charcoal, there was ultimately obtained a clear chloroform solution of the desired final product. Evaporation of the latter solution to near dryness while under reduced pressure then gave a white solid material, which afforded pure 1-cyclohexyl-3-{4-[2-(1,3-dimethyl-1,2,3,4-tetrahydropyrimidine-2,4-dione-5-carboxamido)ethyl]-1-piperidinesulfonyl}urea (m.p. 205°–207° C.) on recrystallization from acetonitrile-methanol. The yield of pure product was 70% of the theoretical value.

Anal. Calcd. for $C_{21}H_{34}N_6O_6S.0.5H_2O$: C, 49.69; H, 6.95; N, 16.56. Found: C, 49.44; H, 6.65; N, 16.58.

EXAMPLE VII

A mixture of 1.7 g. (0.004 mole) of 4-[2-(1-n-propyl-3-ethyl-1,2,3,4-tetrahydropyrimidine-2,4-dione-5-carboxamido)ethyl]-1-piperidinesulfonamide, 1.6 g. (0.005 mole) of 1,1-diphenyl-3-(bicyclo[2.2.1]hept-5-en-2-yl-endo-methyl)urea and 0.23 g. (0.005 mole) of 56% sodium hydride (in mineral oil) in 20 ml. of dry N,N-dimethylformamide was heated at 65° C. for a period of 1.5 hours. At the end of this time, a homogenous yellow solution was obtained which was subsequently cooled and poured into 150 ml. of dry diethyl ether. The white crystalline solid which separated at this point was the crude sodium salt of 1-(bicyclo[2.2.1]hept-5-en-2-yl-endo-methyl)-3-{4-[2-(1-n-propyl-3-ethyl-1,2,3,4-tetrahydropyrimidine-2,4-dione-5-carboxamido)ethyl]-1-piperidinesulfonyl}urea. Purification was then accomplished via recrystallization from chloroform-ethyl acetate to give 0.94 g. of a white, hygroscopic compound which melted at 143° C. with decomposition. The yield of pure product was 39.6% of the theoretical value.

Anal. Calcd. for $C_{26}H_{39}N_6O_6SNa.2H_2O$: C, 50.06; H, 6.24; N, 13.48 Found: C, 49.98; H, 6.42; N, 13.22.

EXAMPLE VIII

A mixture of 380 mg. (0.001 mole) of 4-[2-(1,3-dimethyl-1,2,3,4-tetrahydropyrimidine-2,4-dione-5-carboxamido)ethyl]-1-piperidinesulfonamide, 220 mg. (0.001 mole) of 1-adamantyl isocyanate and 310 mg. (0.002 mole) of anhydrous potassium carbonate in 30 ml. of acetone was refluxed for a period of 20 hours. At the end of this time, the spent reaction mixture was cooled and the excess potassium carbonate subsequently removed therefrom by means of suction filtration. The resulting filtrate was then slowly acidified with 1N aqueous hydrochloric acid causing a white precipitate to form. The latter material was subsequently recovered by suction filtration and thereafter recrystallized from acetonitrile-methanol to afford 220 mg (38%) of pure 1-(1-adamantyl)3-{4-[2-(1,3-dimethyl-1,2,3,4-tetrahydropyrimidine-2,4-dione-5-carboxamido)ethyl]-1-piperidinesulfonyl}urea, m.p. 224°–226° C.

Anal. Calcd. for $C_{25}H_{38}N_6O_6S.H_2O$: C, 52.80; H, 7.09; H, 14.78. Found: C, 52.76; H, 6.43; N, 14.96.

EXAMPLE IX

A mixture consisting of 1.12 g. (0.003 mole) of 4-[2-(1,3-dimethyl-1,2,3,4-tetrahydropyrimidine-2,4-dione-5-carboxamido)ethyl]-1-piperidinesulfonamide, 1.35 g. (0.004 mole) of 1,1-diphenyl-3-(7-oxabicyclo[2.2.1]hept-2-yl-endo-methyl)urea and 0.19 g. (0.004 mole) of 56% sodium hydride (in mineral oil) in 10 ml. of dry N,N-dimethylformamide was stirred at ambient temperature for a period of 18 hours. The resulting mixture was then poured into 200 ml. of anhydrous diethyl ether to yield a white-colored gum that was subsequently recovered by means of decantation and washed twice with fresh diethyl ether. The gum was then dissolved in 1N aqueous hydrochloric acid and the latter aqueous solution extracted with chloroform, followed by separation of the organic layer and drying over anhydrous magnesium sulfate. After decolorizing the organic (chloroform) solution with charcoal and filtering, there was obtained a clear solution which was subsequently evaporated to near dryness while under reduced pressure to afford a pale yellow-colored oil. Crystallization of the latter material from acetonitrile then gave (after three recrystallizations) pure 1-(7-oxabicyclo[2.2.1]hept-2-ylendo-methyl)-3-{4-[2-(1,3-dimethyl-1,2,3,4-tetrahydropyrimidine-2,4-dione-5-carboxamido)ethyl]-1-piperidinesulfonyl}urea in the form of white crystals melting at 217°-218° C. The yield of pure product was 20% of the theoretical value.

Anal. Calcd. for $C_{22}H_{34}N_6O_7S$: C, 50.18; H, 6.51; N, 15.96. Found: C, 49.97; H, 6.51; N, 15.66.

EXAMPLE X

The following 1-piperidinesulfonylureas are prepared by employing the procedures described in the previous sulfamylurea examples (viz., Examples IV–IX), starting from the corresponding sulfamide and the appropriate organic isocyanate or 1,1-diphenyl-3-substituted urea in each instance:

| R | $R_1$ | $R_2$ |
|---|---|---|
| $CH_3$ | $CH_3$ | cyclopentyl |
| $C_2H_5$ | n-$C_3H_7$ | cyclohexyl |
| $C_2H_5$ | $CH_3$ | cycloheptyl |
| iso-$C_3H_7$ | $CH_3$ | cyclooctyl |
| $CH_3$ | $C_2H_5$ | bicyclo[2 . 2 . 1]hept-5-en-2-yl-endo-methyl |
| $C_2H_5$ | $C_2H_5$ | bicyclo[2 . 2 . 1]hept-2-yl-endo-methyl |
| n-$C_3H_7$ | $C_2H_5$ | 7-oxabicyclo[2 . 2 . 1]hept-2-yl-endo-methyl |
| $CH_3$ | iso-$C_3H_7$ | 1-adamantyl |
| n-$C_3H_7$ | n-$C_3H_7$ | cyclopentyl |
| $CH_3$ | $CH_3$ | cycloheptyl |
| $C_2H_5$ | n-$C_3H_7$ | cyclooctyl |
| n-$C_3H_7$ | n-$C_3H_7$ | bicyclo[2 . 2 . 1]hept-5-en-2-yl-endo-methyl |
| n-$C_3H_7$ | n-$C_3H_7$ | bicyclo[2 . 2 . 1]hept-2-yl-endo-methyl |
| $CH_3$ | $C_2H_5$ | 7-oxabicyclo[2 . 2 . 1]hept-2-yl-endo-methyl |
| $C_2H_5$ | $C_2H_5$ | 1-adamantyl |
| n-$C_3H_7$ | $C_2H_5$ | cyclopentyl |
| n-$C_3H_7$ | n-$C_3H_7$ | cyclohexyl |
| n-$C_3H_7$ | n-$C_3H_7$ | cycloheptyl |
| $CH_3$ | $CH_3$ | cyclooctyl |
| $C_2H_5$ | n-$C_3H_7$ | bicyclo[2 . 2 . 1]hept-5-en-2-yl-endo-methyl |
| $CH_3$ | iso-$C_3H_7$ | bicyclo[2 . 2 . 1]hept-2-yl-endo-methyl |
| iso-$C_3H_7$ | $CH_3$ | 7-oxabicyclo[2 . 2 . 1]hept-2-yl-endo-methyl |
| n-$C_3H_7$ | n-$C_3H_7$ | 1-adamantyl |
| $C_2H_5$ | n-$C_3H_7$ | cyclopentyl |
| $CH_3$ | iso-$C_3H_7$ | cyclohexyl |
| n-$C_3H_7$ | n-$C_3H_7$ | cyclooctyl |

EXAMPLE XI

A solution consisting of 338.4 g. (0.72 mole) of 1-(bicyclo-[2.2.1]hept-5-en-2-yl-endo-methyl)-3-{4-[2-(1,3-dimethyl-1,2,3,4-tetrahydropyrimidine-2,4-dione-5-carboxamido)ethyl]-1-piperidinesulfonyl}urea dissolved in 2.0 liters of methanol was treated at 0° C. with 38.9 g. (0.72 mole) of sodium methoxide divided into five separate portions. The reaction mixture was then concentrated in vacuo and the resulting residue thereafter recrystallized from 7.0 liters of acetonitrile to give a nearly quantitative yield of product, viz., the sodium salt of 1-(bicyclo[2.2.1]hept-5-en-2-yl-endo-methyl)-3-{4-[2-(1,3-dimethyl-1,2,3,4-tetrahydropyrimidine-2,4-dione-5-carboxamido)ethyl]-1-piperidinesulfonyl}urea, m.p. 153°-190° C.

Anal. Calcd. for $C_{23}H_{33}N_6O_6SNa.1.5H_2O$: C, 48.32; H, 5.82; N, 14.72. Found: C, 48.40; H, 5.73; N, 14.52.

EXAMPLE XII

The sodium salt of 1-(bicyclo[2.2.1]hept-5-en-2-yl-endo-methyl)-3-{4-[2-(1-n-propyl-3-ethyl-1,2,3,4-tetrahydropyrimidine-2,4-dione-5-carboxamido)ethyl]-1-piperidinesulfonyl}urea is prepared by dissolving said compound in anhydrous methanol and then adding said solution to another methanolic solution which contains an equivalent amount in moles of sodium methoxide. Upon subsequent evaporation of the solvent therefrom via freeze-drying, there is obtained the desired alkali metal salt in the form of an amorphous solid power which is freely soluble in water.

In like manner, the potassium and lithium salts are also similarly prepared, as are the alkali metal salts of all the other acidic 1-piperidinesulfonylureas of this invention which are reported in the previous examples.

EXAMPLE XIII

The calcium salt of 1-cyclohexyl-3-{4-[2-(1,3-dimethyl-1,2,3,4-tetrahydropyrimidine-2,4-dione-5-carboxamido)ethyl]-1-piperidinesulfonyl}urea is prepared by dissolving said compound in water containing an equivalent amount in moles of calcium hydroxide and then freeze-drying the mixture. The corresponding magnesium salt is also prepared in like manner, as are all the other alkaline-earth metal salts not only of this particular compound, but also of those acidic 1-piperidinesulfonyl-ureas previously described in Examples IV–V and VII–IX, respectively.

EXAMPLE XIV

A dry solid pharmaceutical composition is prepared by blending the following materials together in the proportions by weight specified below:

| | |
|---|---|
| 1-(Bicyclo[2 . 2 . 1]hept-5-en-2-yl-endo-methyl)-3-{4-[2-(1,3-dimethyl-1,2,3,4-tetrahydropyrimidine-2,4-dione-5-carboxamido)ethyl]-1-piperidinesulfonyl}urea | 50 |
| Sodium citrate | 25 |
| Alginic acid | 10 |
| Polyvinylpyrrolidone | 110 |
| Magnesium stearate | 5 |

After the dried composition is thoroughly blended, tablets are punched from the resulting mixture, each tablet being of such size that it contains 75 mg. of the active ingredient. Other tablets are also prepared in a similar fashion containing 5, 10, 25 and 50 mg. of the active ingredient, respectively, by merely using the appropriate amount of the 1-piperidinesulfonylurea in each case.

EXAMPLE XV

A dry solid pharmaceutical composition is prepared by combining the following materials together in the proportions by weight indicated below:

| | |
|---|---|
| 1-Cyclohexyl-3-{4-[2-(1,3-dimethyl-1,2,3,4-tetrahydropyrimidine-2,4-dione-5-carboxamido)ethyl]-1-piperidinesulfonyl}urea | 50 |
| Calcium carbonate | 20 |
| Polyethylene glycol, average molecular weight, 4000 | 30 |

The dried solid mixture so prepared is then thoroughly agitated so as to obtain a powdered product that is completely uniform in every respect. Soft elastic and hard-filled gelatin capsule containing this pharmaceutical composition are then prepared, employing a sufficient quantity of material in each instance so as to provide each capsule with 125 mg. of the active ingredient.

EXAMPLE XVI

The 1-piperidinesulfonylurea final products of Examples IV-IX were tested for hypoglycemic activity in groups of six male albino rats (each weighing approximately 190-240 g.) of the Sprague-Dawley strain. No anesthetic was used in this study. The rats were fasted for approximately 18-24 hours prior to administration, a blood sample was then taken from the tail vein of each animal and the test compound was administered intraperitoneally (while in solution as the sodium salt in 0.9% saline) at dose levels of 15, 5.0 and 1.0 mg./kg., respectively. Additional blood samples were then take at 1, 2 and 4 hour intervals after administration of the drug. The samples were immediately diluted 1:10 (by volume) with 1.0% heparin in 0.9% saline. Blood glucose was determined by adapting the method of W. S. Hoffman [Journal of Biological Chemistry, Vol. 120, p. 51 (1937)] to the Autoanalyzer instrument produced by Technicon Instruments Corporation of Chauncey, N.Y. On this basis, the maximum percent decrease in blood sugar was calculated and reported as such (i.e., as hypoglycemic activity) for the various compounds listed in the table below:

| 1-Piperidine- | Hypoglycemic Activity (Max.% Fall) | | |
| --- | --- | --- | --- |
| sulfonylurea | 1.0mg./kg. | 5.0mg./kg. | 15mg./kg. |
| Product of Example IV | 5.5 | 21 | — |
| Product of Example V | — | 19 | — |
| Product of Example VI | — | — | 29 |
| Product of Example VII | — | 13 | — |
| Product of Example VIII | — | 19 | — |
| Product of Example IX | — | — | 13 |

What is claimed is:

1. A method for lowering blood sugar in the treatment of a diabetic animal, which comprises orally administering to said animal an effective blood sugar lowering amount of a compound selected from a group consisting of 1-piperidinesulfonylureas of the formula:

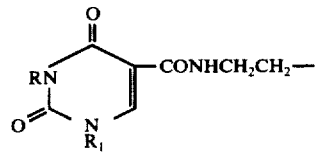

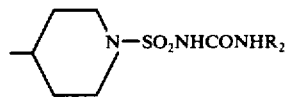

and the base salts thereof with pharmacologically acceptable cations, wherein R and $R_1$ are each alkyl having from one to three carbon atoms, and $R_2$ is a member selected from the group consisting of bicyclo[2.2.1]-hept-5-en-2-yl-endo-methyl, bicyclo[2.2.1]hept-2-yl-endo-methyl, 7-oxabicyclo[2.2.1]hept-2-yl-endomethyl, 1-adamantyl and cycloalkyl having from five to eight carbon atoms.

2. The method as claimed in claim 1 wherein the compound administered is 1-(bicyclo[2.2.1]hept-5-en-2-yl-endo-methyl)-3-{4-[2-(1,3-dimethyl-1,2,3,4-tetrahydropyrimidine-2,4-dione-5-carboxamido)ethyl]-1-piperidinesulfonyl}urea.

3. The method as claimed in claim 1 wherein the compound administered is 1-(bicyclo[2.2.1]hept-2-yl-endo-methyl)-3-{4-[2-(1,3-dimethyl-1,2,3,4-tetrahydropyrimidine-2,4-dione-5-carboxamido)ethyl]-1-piperidinesulfonyl}urea.

4. The method as claimed in claim 1 wherein the compound administered is 1-(1-adamantyl-3-{4-[2-(1,3-dimethyl-1,2,3,4-tetrahydropyrimidine-2,4-dione-5-carboamido)ethyl]-1-piperidinesulfonyl}urea.

5. The method as claimed in claim 1 wherein the compound administered is 1-cyclohexyl-3-{4-[2-(1,3-dimethyl-1,2,3,4-tetrahydropyrimidine-2,4-dione-5-carboxamido)ethyl]-1-piperidinesulfonyl}urea.

6. The method as claimed in claim 1 wherein the compound administered is 1-(bicyclo[2.2.1]hept-5-en-2-yl-endo-methyl)-3-{4-[2-(1-n-propyl-3-ethyl-1,2,3,4-tetrahydropyrimidine-2,4-dione-5-carboxamido)ethyl]-1-piperidinesulfonyl}urea.

7. An oral hypoglycemic pharmaceutical composition comprising a pharmaceutically acceptable carrier and an effective blood sugar lowering amount of an oral hypoglycemic agent selected from the group consisting of 1-piperidinesulfonylureas of the formula:

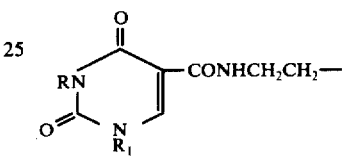

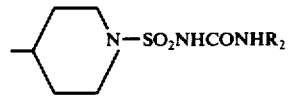

and the base salts thereof with pharmacologically acceptable cations, wherein R and $R_1$ are each alkyl having from one to three carbon atoms, and $R_2$ is a member selected from the group consisting of bicyclo[2.2.1]-hept-5-en-2-yl-endo-methyl, bicyclo[2.2.1]hept-2-yl-endo-methyl, 7-oxabicyclo[2.2.1]hept-2-yl-endomethyl, 1-adamantyl and cycloalkyl having from five to eight carbon atoms.

8. The composition according to claim 7 wherein the hypoglycemic agent is 1-(bicyclo[2.2.1]hept-5-en-2-yl-endomethyl)-3-{4-[2-(1,3-dimethyl-1,2,3,4-tetrahydropyrimidine-2,4-dione-5-carboxamido)ethyl]-1-piperidinesulfonyl}urea.

9. The composition according to claim 7 wherein the hypoglycemic agent is 1-(bicyclo[2.2.1]hept-2-yl-endomethyl)-3-{4-[2-(1,3-dimethyl-1,2,3,4-tetrahydropyrimidine-2,4-dione-5-carboxamido)ethyl]-1-piperidinesulfonyl}urea.

10. The composition according to claim 7 wherein the hypoglycemic agent is 1-(1-adamantyl-3-{4-[2-(1,3-dimethyl-1,2,3,4-tetrahydropyrimidine-2,4-dione-5-carboxamido)ethyl]-1-piperidinesulfonyl}urea.

11. The composition according to claim 7 wherein the hypoglycemic agent is 1-cyclohexyl-3-{4-[2-(1,3-dimethyl-1,2,3,4-tetrahydropyrimidine-2,4-dione-5-carboxamido)ethyl]-1-piperidinesulfonyl}urea.

12. The composition according to claim 7 wherein the hypoglycemic agent is 1-(bicyclo[2.2.1]hept-5-en-2-yl-endo-methyl)-3-{4-[2-(1-n-propyl-3-ethyl-1,2,3,4-tetrahydropyrimidine-2,4-dione-5-carboxamido)ethyl]-1-piperidinesulfonyl}urea.

* * * * *